United States Patent [19]
Brain

[11] Patent Number: 5,241,956
[45] Date of Patent: Sep. 7, 1993

[54] LARYNGEAL MASK AIRWAY WITH CONCENTRIC DRAINAGE OF OESOPHAGUS DISCHARGE

[76] Inventor: Archibald I. J. Brain, St. Andrews, Abney Court Drive, Bourne End, Bucks, United Kingdom

[21] Appl. No.: 952,586

[22] Filed: Sep. 28, 1992

Related U.S. Application Data

[63] Continuation-in-part of Ser. No. 919,289, Jul. 24, 1992.

[30] Foreign Application Priority Data

May 21, 1992 [GB] United Kingdom ............... 9210854
Jul. 23, 1992 [GB] United Kingdom ............... 9215650

[51] Int. Cl.$^5$ ............................................. A61M 16/00
[52] U.S. Cl. ........................... 128/207.15; 128/207.14; 604/174; 604/96
[58] Field of Search ............... 128/207.14, 207.15, 128/206.26, 207.16, 200.26; 604/96–103, 174

[56] References Cited

U.S. PATENT DOCUMENTS

| | | | |
|---|---|---|---|
| 4,454,887 | 6/1984 | Krüger | 128/772 |
| 4,497,318 | 2/1985 | Donmichael | 128/202.28 |
| 4,969,458 | 11/1990 | Wiktor | 606/194 |
| 4,981,470 | 1/1991 | Bombeck, IV | 128/635 |
| 4,995,388 | 2/1991 | Brain | 128/207.15 |
| 5,033,466 | 7/1991 | Weymuller | 128/207.15 |
| 5,038,766 | 8/1991 | Parker | 128/200.26 |
| 5,067,497 | 11/1991 | Greear | 128/207.15 |
| 5,076,268 | 12/1991 | Weber | 128/207.15 |
| 5,116,305 | 5/1992 | Milder | 600/18 |

FOREIGN PATENT DOCUMENTS

| | | | |
|---|---|---|---|
| 2111394 | 7/1983 | United Kingdom | 128/207.15 |
| 2171017 | 8/1986 | United Kingdom | 128/207.15 |
| 2229367 | 9/1990 | United Kingdom | 128/207.15 |

*Primary Examiner*—Edgar S. Burr
*Assistant Examiner*—Eric P. Raciti
*Attorney, Agent, or Firm*—Hopgood, Calimafde, Kalil, Blaustein & Judlowe

[57] ABSTRACT

A laryngeal mask airway is described which is fitted with an evacuation or drainage tube which passes through the back of the mask and terminates concentrically within an inflatable-cuff formation at the distal end of the mask. In the case of a laryngeal mask which relies on an inflatable ring to establish a seal around the laryngeal inlet, the inflatable-cuff formation results from sealed passage of the evacuation tube through the distal region of the inflatable ring, the distal end of which is centrally apertured and reentrantly folded into sealed junction with the distal end of the tube. When the mask is inflated, its distal end establishes a cuff, sealing the tube against the upper oesophageal sphincter. In the presently preferred embodiment, an auxiliary inflatable cuff is carried at the back side of the mask and, when inflated, establishes a cushioned reference between the evacuation tube and the posterior wall of the pharynx, enabling more effective sealing of the mask to the laryngeal inlet and of the drainage cuff to the oesophageal sphincter, in the circumstance of negative pressure applied to the evacuation tube.

19 Claims, 3 Drawing Sheets

LARYNGEAL MASK AIRWAY WITH CONCENTRIC DRAINAGE OF OESOPHAGUS DISCHARGE

RELATED CASE

This application is a continuation-in-part of my pending application Ser. No. 07/919,289, filed Jul. 24, 1992.

BACKGROUND OF THE INVENTION

The invention relates to laryngeal masks, illustratively of the varieties disclosed in U.K. Patent 2,111,394B (corresponding to U.S. Pat. No. 4,509,514) and in published U.K. Patent Application No. 2,229,367A (corresponding to U.S. Pat. No. 4,995,388). Such masks are artificial airway devices designed to facilitate lung ventilation in an unconscious patient by forming a low-pressure seal around the laryngeal inlet. A seal surrounds an appropriately shaped mask which fits into the lower pharynx and is attached to a tube which emerges from the mouth, as for connection to medical gas-supply tubing.

In practice, these devices have been successful and are now in daily use in hospitals throughout the United Kingdom. Such masks have been found effective in achieving a reliable airway, preventing obstruction in the unconscious patient. As presently used, such masks are especially effective in cases where difficulty with the airway is experienced. For example, the mask has been found to prevent contamination of the lungs by blood or debris during surgery of the nose or throat. But it has become apparent that an important contraindication to its use is the patient who is at risk from vomiting or regurgitation of stomach contents while unconscious. Although the device forms an inflatable-cuff seal around the laryngeal inlet sufficient to permit inflation of the lungs during artificial ventilation, the seal is not sufficient to prevent lung contamination in the event of retching, vomiting or regurgitation. Patients who are not adequately starved prior to surgery are thus not suitable for use of the laryngeal mask. In such patients, an endotracheal tube is still regarded as affording the safest protection to the patient's airways. However, insertion of an endotracheal tube is not always without difficulty, and failure to make a timely insertion can lead to death or brain damage. In such cases, the laryngeal mask has proven to be life-saving. And, in cases when it has not been possible to safely insert an endotracheal tube, it has been found possible first to install a laryngeal mask, and then to use the tube of the laryngeal mask as a guide, for piloted insertion of an endotracheal tube through the mask.

My U.S. Pat. No. 4,995,388 describes other means associated with a laryngeal mask to prevent aspiration of stomach contents into the lungs. In essence, such means rely upon a combination of improved peripheral continuity of seal pressure against the larynx and the provision of drainage tubing for conduct of gastric contents away from the laryngeal inlet.

Regardless of the specific purpose to be achieved with laryngeal masks in use today, the problem of sealing effectiveness persists, in respect of assuring against entry of a gastric discharge in the laryngeal inlet. My U.S. Pat. No. 4,995,388 describes laryngeal-mask configurations with three different embodiments to facilitate drainage of gastric contents behind the mask. In one of these embodiments a drainage tube passes directly into the oesophagus; in a second of these embodiments, a drainage tube is forked anteriorly of the mask, with drainage openings on both sides of the mask bowl; and in the third embodiment, the drainage tube passes behind the mask to terminate alongside the mask tip.

But each of these three embodiments has been found to be less than satisfactory, for one or more reasons. The disadvantage of the first embodiment is that it is more invasive and breaks the seal which a non-draining inflatable mask establishes at the upper oesophageal sphincter. The disadvantage of the second embodiment is that the drainage provision is so positioned that it will draw off regurgitated fluid only after it has already entered the bowl of the mask, thus risking entry into the trachea of at least some of this fluid. And the disadvantage of the third embodiment is that it must be truncated diagonally at its tip to facilitate mask insertion, thus presenting an elliptical opening behind the mask tip, so that mask inflation tends to press this opening against the wall of the pharynx, thereby blocking the opening and impairing the desired drainage function.

Aside from the difficulties noted above in respect of proposals for preventing gastric contents from entry into the laryngeal inlet, it is important to note some of the environmental problems encountered by a laryngeal mask, however well-designed for accuracy of fit to the lower pharynx, so that when inflated, pressure is exerted on all surrounding structures, to greater or lesser degrees, depending on the resistance they offer to displacement. In broad terms, the structures in front of the mask are cartilaginous; those surrounding the mask are muscular; and those behind the mask are bony. Inflation of the cuff of the mask therefore results in the cartilaginous structures of the larynx being pushed forward, away from the bony structures of neck vertebrae, thus stretching and tensing the surrounding muscles. The seal generated against the laryngeal inlet therefore depends to some extent upon stretch resistance of muscles and soft tissues, as cuff-inflating volume of the mask expands.

If an unconscious patient retches, vomits or regurgitates gastric contents, the balance of forces reacting on the inflated cuff is transiently upset. The muscles surrounding the mask relax, and the sphincteric mechanism at the lower end of the mask also relaxes, with consequent loss or degrading of seal effectiveness; and fluid or semisolids can be forced upward through the oesophagus during such relaxation. Moreover, the larynx is itself displaced upwards as part of the vomiting or retching reflex, and such displacement alone may be sufficient to disrupt the seal of the mask around the laryngeal inlet.

Still further, and of crucial importance, is the fact that the airway tube to which the mask is attached offers resistance to flexure when in its normal position in the patient's pharynx. The airway tube thus exerts a constant force against the bony posterior walls of the pharynx. This means that in the event of a relaxation of the surrounding structures, the mask will tend to remain firmly in contact with the posterior wall. Vomited or regurgitated matter may therefore pass in front of the mask and so enter the laryngeal inlet.

BRIEF STATEMENT OF THE INVENTION

It is an object of the invention to provide a laryngeal-mask system with improved ability to prevent lung soiling by gastric contents.

It is a specific object of the invention to achieve the above object by providing a gastric-drainage feature for such a mask system, wherein the drainage feature is in such sealed relation to the upper sphinctral region of the oesophagus as to materially reduce the risk of any gastric-discharge entry into the laryngeal inlet.

Stated in other words, it is a specific object to achieve such effectiveness in the sealed relation of the drainage feature to the upper sphinctral region as to assure that gastric-drainage will be virtually independent of transient loss of seal effectiveness around the laryngeal inlet, as may be occasioned by changes in surrounding structures during vomiting, retching or regurgitation.

Another specific object is to achieve the above objects with a sealed drainage feature in which it can at all times be observable whether the drainage seal remains intact.

It is also a specific object to provide a laryngeal mask system with a gastric-drainage feature that avoids the noted difficulties of prior drainage systems.

Still another specific object to meet the above objects with a gastric-drainage feature which involves minimum entry into the upper sphinctral region and which therefore presents minimum risk of trauma to the oesophagus.

A general object is to achieve the foregoing objects with relatively simple structure which is of minor incremental cost and which is readily and effectively usable, even in the hands of relatively unskilled paramedic personnel.

The invention in a first preferred embodiment achieves these objects in a laryngeal-mask system of the character indicated wherein the inflatable generally elliptical annular ring of the mask is provided with an evacuation-tube which is open through the center of the distal end of the inflatable ring, thus utilizing the distal end of the inflatable ring as an inflatable cuff formation which (a) establishes peripherally sealed engagement to the upper sphinctral region of the oesophagus, (b) centrally and resiliently supports the distal end of the evacuation tube, and (c) which, in the normal condition of operating under reduced pressure for evacuation purposes, will inherently draw tissues adjacent the distal-cuff formation into enhanced oesophageal-sealing effectiveness, thus effectively tightening the sphincter.

In another preferred embodiment, inflatable-cuff structure is additionally incorporated in at least a portion of the backside of the mask. This additional structure is of softer material than that of the inflatable generally elliptical annular ring of the mask. The additional structure inflates to establish a soft profile-conforming reference to the bony posterior wall of the pharynx, for gentle application of forwardly directed loading of the inflatable mask around the laryngeal inlet. As a result, inflation pressure to establish seal action around the laryngeal inlet can be at substantially reduced levels, enabling an enhanced sealing effectiveness of the mask around the laryngeal inlet. This enhanced seal action is achieved without detriment to seal engagement to the upper sphinctral region of the oesophagus, for gastric-drainage purposes noted above.

DETAILED DESCRIPTION OF THE INVENTION

The invention will be described in detail for a preferred embodiment and for other embodiments, all in conjunction with the accompanying drawings, in which.

Referring first to the preferred embodiment of FIGS. 1 to 4, the invention is shown in application to an airway system comprising a laryngeal-mask unit 10 and its airway tube 11 which is installed through the mouth 12 of a patient. The mask unit 10 may be generally as described in either of said U.S. patents and therefore need not now be described in detail. It suffices to say that mask unit 10 comprises a body portion 13 having a lumen 14 through which the airway tube 11 can establish a free externally accessible ventilating passage, via the patient's mouth 12 and throat 15, and past the epiglottis 16 to the larynx 17. The body 13 of mask 10 may be of silicone rubber and relatively stiff: and body 13 is surrounded by an inflatable ring 18 which is generally elliptical and which is circumferentially united to body 13 in essentially a single plane. The inflatable ring 18 may also be of silicone rubber, although preferably relatively soft and flexible compared to body 13. An externally accessible flexible tube 19 is the means of supplying air to the inflatable ring 18 and of extracting air from (and therefore collapsing) ring 18 for purposes of mask insertion in or removal from the patient; check-valve means 21 in tube 19 will be understood to hold a given inflation or to hold a given deflation of ring 18. In the installed position of FIG. 1, the projecting but blunted distal end 20 of ring 18 is shaped to conform with the base of the hypopharynx where it has established locating limited entry into the upper sphinctral region of the oesophagus 24. The inflated ring establishes a peripherally sealed closure around the laryngeal inlet, orienting the axis of the distal end of the airway tube 11 at an acute angle to the general plane of ring 18 and in substantial alignment with the axis of the laryngeal inlet, for direct airway communication only with the larynx 17.

Figures 1, 2, 3, 4:
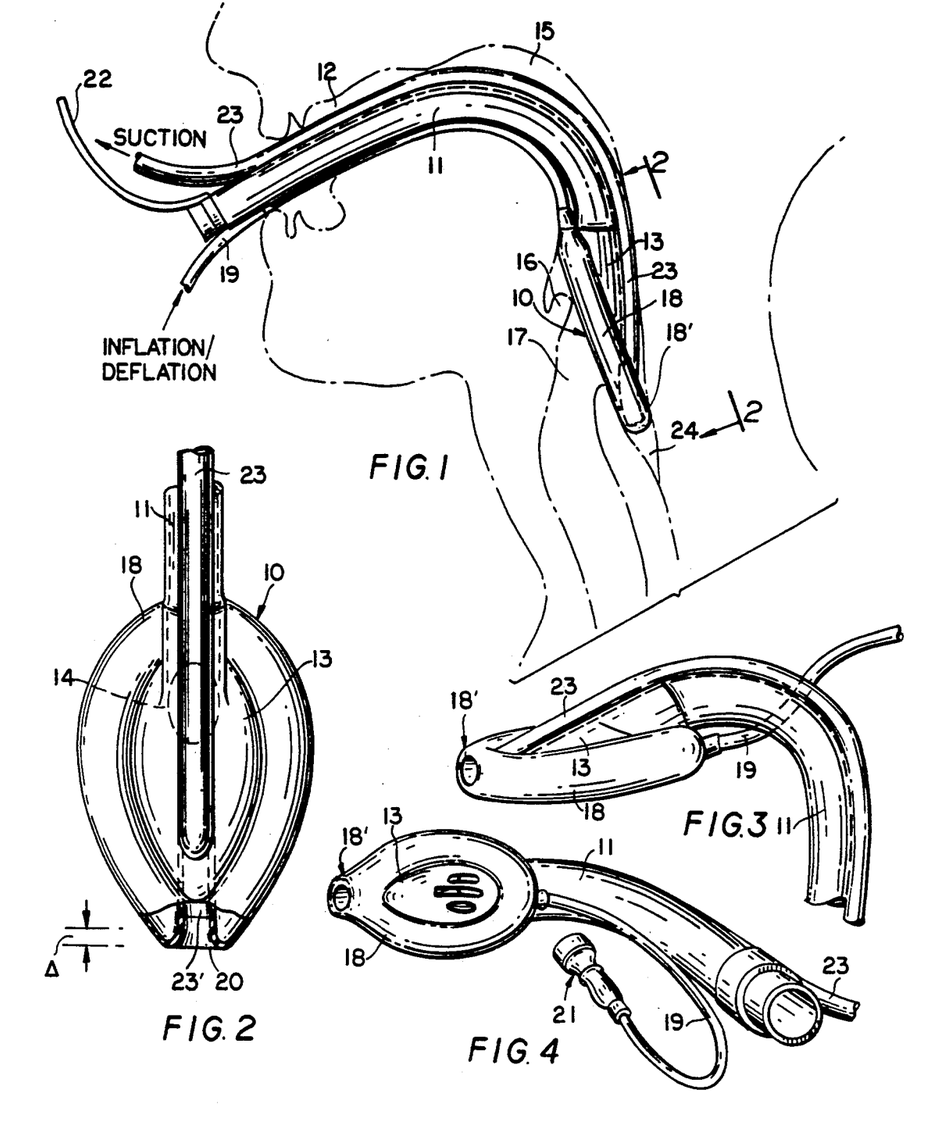
FIG. 1 is a diagrammatic view, generally in side elevation for a first preferred embodiment of an artificial-airway device, having a laryngeal mask with a gastric-drainage feature of the invention, the same being shown in position for use in a patient.
FIG. 2 is an enlarged fragmentary view of the mask portion of FIG. 1, as seen from the aspect 2—2 of FIG. 1.
FIG. 3 is a perspective view of the device of FIG. 1, from a first distal-quarter aspect which reveals the posterior side of the laryngeal mask.
FIG. 4 is another perspective view of the device of FIG. 1, from a second distal-quarter aspect which reveals the anterior side of the laryngeal mask.

In accordance with the invention, provision is made for an evacuation tube 23 to follow the general course of the airway tube 11, with sealed entry of the airway tube into the mask body 13 and passage through the interior of ring 18 near the distal end of the mask. As seen in FIG. 2, the open distal end of the airway tube 23 is sealed to reentrant soft material of ring 18 at a distal central piercing of ring 18, such that (a) the distal end of tube 23 is concentrically supported by and within the upper sphinctral region when inflated, and (b) the distal end 23 of tube 23 will be at small offset behind the distal thus-blunted end of ring 18. Stated in other words, the described structural arrangement establishes a circumferentially continuous flexible annulus or cuff formation at the distal end of ring 18 for softly but concentrically stabilized support of the distal-end of tube 23, all in peripherally sealed engagement to tissues of the upper sphinctral region. Since passage of evacuation tube 23 through the inflated inner volume of ring 18 necessarily means that tube 23 will be subject to a crushing pressure equal to the inflation pressure of ring 18, plus the reduced pressure relied upon for suction to evacuate any discharge of gastric products, the tube 23 should be suitably reinforced or at least of structural strength to withstand such crushing pressure; in this connection, commercial plastic tubing having an internal diameter of 5–10 mm and lined with a reinforcing continuous helix of fine stainless steel wire is satisfactory.

Figure 5:
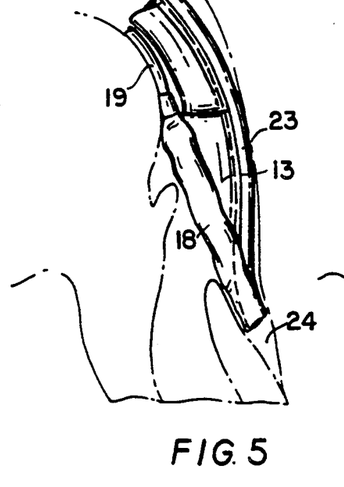
FIG. 5 is an enlarged fragmentary view in side elevation, illustrative of the deflated condition of the cuff formation, in relation to the upper sphinctral region of the oesophagus.
Figure 5A:
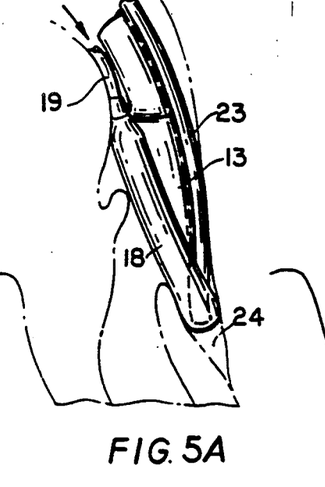
FIG. 5A is a view similar to FIG. 5, to show the inflated-cuff formation and its relation to the upper sphinctral region.
Figure 5B:
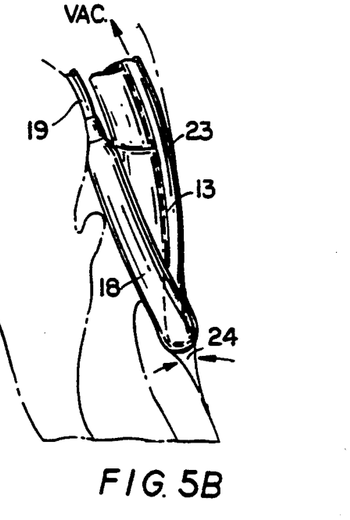
FIG. 5B is another view similar to FIG. 5, to show the inflated-cuff formation and its relation to adjacent tissues of the upper sphinctral region, when under the reduced pressure of gastric-evacuating suction.

Action of the described mask and drainage/evacuation tube 23 will be better understood from the succession of diagrams of FIGS. 5, 5A and 5B. In FIG. 5, the relation is that of the mask having just been inserted into the patient, while ring 18 is fully deflated, so that the stubby distal end of the mask has been able to enter the upper sphinctral region, with less than sealing engagement to said region. However, once inserted, inflation air should be introduced via the inflation/deflation tube 19, typically to a pressure in the range between 80 and 160-mm Hg, so that the mask installation has the appearance depicted in FIG. 5A; specifically, at this juncture, ring 18 has not only developed its sealed engagement around the laryngeal inlet, but the cuff-like formation 18' at the distal end of the mask has expanded into resiliently adapted circumferentially continuous preliminarily sealed engagement with adjacent tissues of the upper sphinctral region. Should tube 23 be under evacuation, the reduced pressure from a suction device (not shown) at the external end of tube 23 will subject the oesophagus to the reduced pressure, causing adjacent tissues to deform into a greater area of sealing the upper sphinctral region to the bulbous inflated end 18', resulting in the relation depicted in FIG. 5B.

It is recommended that a simple small-displacement spring-return bellows (not shown) be first compressed against spring-return action, to expel the air from its normally expanded volume, that the compressed bellows be then connected to the externally exposed end of tube 23, and that the spring compression should then be released to allow spring-return action to induce a suction in tube 23. A proper positioning of mask 10 is then noted if the bellows fails to expand fully under the force of spring-return action, because the oesophagus will then have been assuredly sealed off from communication with the laryngeal inlet. Having this assurance of proper seal action, the bellows can be in place as a continuous monitor; alternatively, the bellows can be replaced with a suitably monitored and controlled connection to locally available suction means.

Figures 6, 8:
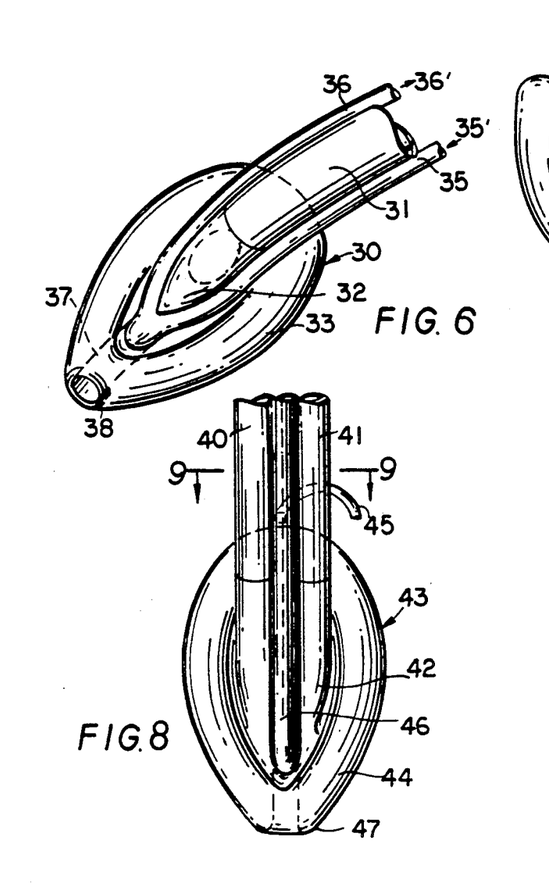
FIG. 6 is a fragmentary perspective view of another embodiment of the invention, as seen from a distal-quarter aspect which reveals the posterior side of an involved laryngeal mask.
FIG. 8 is generally a fragmentary plan view of the posterior side of a further embodiment of the invention.
Figure 7:
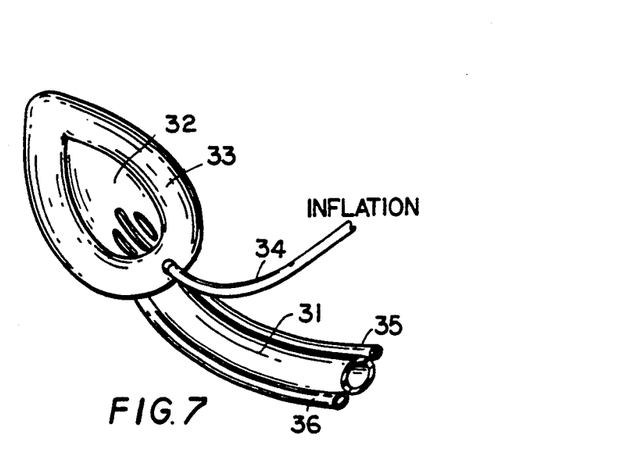
FIG. 7 is another fragmentary perspective view of the embodiment of FIG. 6, as seen from a distal-quarter aspect which reveals the anterior side of the mask.

In the embodiment of FIGS. 6 and 7, a mask 30, having a connection to an airway tube 31 as in FIGS. 1 to 5, also has a relatively stiff body 32, peripherally surrounded by a soft flexible ring 33 that is selectively inflated or deflated via an externally accessible inflation tube 34. Provision for evacuation or drainage of gastric products involves two like tubes 35, 36 which conform to and are carried by airway tube 31. Tubes 35, 36 are the bifurcated arms of a single evacuation tube formation 37 extending through the body and the distal end of ring 33, with centrally sealed connection to the reentrant fold of centrally pierced ring-33 material into overlap with the distal end of tube formation 37, thus establishing the stubby cuff-like formation 38 at the distal end of mask 30.

Action and use of the embodiment of FIGS. 6 and 7 may be as described for FIGS. 1 to 5, provided that both of the tubes 35, 36 are externally connected to a source of sufficient suction action. Alternatively, a steady flow of fluid may be drawn from tube 36, having been thereby induced to flow into the external end of tube 35 (as suggested by arrows 35', 36' in FIG. 6), thereby at the same time aspirating, for external collection, analysis and/or discard, such gastric products as may have entered the single central passage 37. Still further alternatively, an optical or other inspection device (not shown) may have annularly sealed entry into the bifurcation tube 35, as for inspection of the sphinctral region adjacent and near the seal established by the cuff-like formation 38, while the other bifurcation tube 36 is subjected to continuous suction, for extraction of gastric products.

Figure 9:
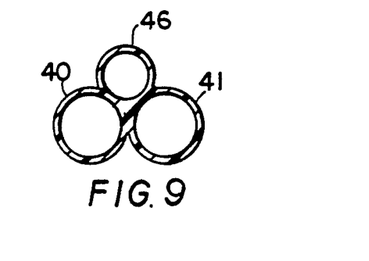
FIG. 9 is an enlarged sectional view, taken at 9—9 in FIG. 8.

In the embodiment of FIGS. 8 and 9, two like airway tubes 40, 41 are in curved, suitably bonded side-by-side adjacency, with connection in common to the body 42 of a single laryngeal mask 43 having an inflation ring 44 and associated inflation/deflation tube connection 45. A single evacuation tube 46 is secured to and along the length of both tubes 40, 41 and has sealed entry into, and passage through ring 44, in the manner previously described for other embodiments, with distal termination centrally open within the upper sphinctral seal established by the cufflike formation 47.

Use of the embodiment of FIGS. 8 and 9 may be as described for the embodiment of FIGS. 1 to 5, except that the addition of another airway tube affords additional options such as accommodation of an optical or other inspection device via one airway tube (40) while the other (41) serves purely airway functions. Alternatively, in conditions of anaesthesia, fresh gases can be breathed in at the level of the larynx by using the tube 40 for fresh-gas delivery, while using the other tube (41) to carry off waste gases (carbon dioxide), thus facilitating the elimination of carbon dioxide.

FIGS. 8 and 9 further serve to illustrate that the three tubes 40, 41, 46 may be the product of a single extrusion, having the section shown in FIG. 9, wherein all three tubes may be of the same internal diameter, or of such relative proportions as to serve particular special-purpose applications. By the same token, the tubes 11 and 23 of FIGS. 1 to 5, and 31, 35, 36 of FIGS. 6 and 7, may also be single extruded products.

The described embodiments of the invention will be seen to afford a number of advantages, including but not limited to the following:

(a) Regurgitant fluid will tend to pass directly into the tubular provision (23, 37, 46) without encountering resistance from the distal tip or end formation of the mask.

(b) Because the distal end of the evacuation tube is centrally within the distal cuff formation, mask or cuff inflation results in an even circumferential swelling around the open distal end of the evacuation tube. This tends to prevent escape of regurgitated fluid around the sides of the mask, even in a retching circumstance, thus substantially reducing the chance of accidental spillage into the larynx.

(c) The oesophagus is a hollow tube which is normally closed. Application of suction to the outer end of the evacuation tube produces a negative pressure at the upper oesophageal sphincter, drawing adjacent tissue walls more tightly together and thus enhancing the seal which is otherwise established by inflation engagement to this sphinctral region. This is an important point because in the anaesthetized state, the sphincter may relax to dangerously low pressures, permitting regurgitation in certain patients.

(d) After laryngeal-mask insertion, it is sometimes unclear where the distal end of the mask has come to rest. It is possible that the distal end of the mask has passed into an undesirable position; for example, it may on occasion pass into the aperture of the larynx, so that it comes to lie against the vocal cords, causing obstruction or damage. Application of negative pressure to the drainage tube, as in point (c) above, will in such circumstances act as a test, since in the incorrect position, air will be drawn out of the trachea, causing gas flow instead of an immediate rise in negative pressure This test (the so called Wee test) already exists for an endotracheal tube to detect malposition in the case that the tube lies in the oesophagus. This test is therefore readily understood by clinicians.

(e) Once in place, the laryngeal mask may be used for positive pressure ventilation of the lungs. However, one of the dangers of this is that excessive pressures applied to the airway via the breathing tube of the laryngeal mask may result in leaks at the mask-to-larynx junction. This is known to result in some cases in gradual inflation of the stomach, which may restrict ventilation and ultimately provoke regurgitation because of increasing intra-gastric pressure. The present invention avoids this danger because not only is the evacuation tube capable of establishing a negative pressure within the oesophagus (thus increasing its seal), but any gas escaping from the mask-to-larynx junction will be siphoned away via the evacuation tube before entering the oesophagus.

A disadvantage of the present invention is that the mask tip is made more bulbous by the presence of the evacuation tube at its distal end, even when fully deflated. This in turn may make it harder to insert without traumatizing or passing into the entrance to the larynx. However, if this invention is used in combination with a rigid tube with handle (Laryngeal Mask Handle as described in my international application No. PCT/GB92/00242 and corresponding to U.S. application Ser. No. 869,491, filed Apr. 20, 1992) in place of the flexible breathing tube of the standard laryngeal mask, reliable insertion becomes easier to achieve. In the embodiment of FIGS. 1 to 5, the airway tube 11 is preferably rigid, as of suitably bent stainless steel, and a handle 22, which may be detachably connected to the outer exposed end of the airway tube serves for better assurance that the inserted distal end of the mask can be steered clear of the anterior structures, for assured entry into the upper sphinctral region In adapting an existing laryngeal mask to the evacuation/drainage purposes of the invention, the tube 23 will be understood to pass through the posterior or "backplate" of the mask body 13, which may conveniently be slit to accept tube 23 or, alternatively, be molded with tube 23 to form a unitary part of it. The curved airway tube 11 which is secured to the mask body 13 is also conveniently adapted to carry the evacuation tube 23 in its posterior or convexly curved wall.

It should also be noted that an installed laryngeal mask, with provision for evacuation of gastric products may serve the further purpose of accurately guiding the insertion of a distally cuffed conventional flexible endotrachial tube, with axially aligned accuracy through the lumen of the mask and into the laryngeal inlet, for subsequent cuff inflation to more assuredly seal the endotrachial tube in substitution for the lung ventilation purposes of such a use.

Figures 10, 11, 12:
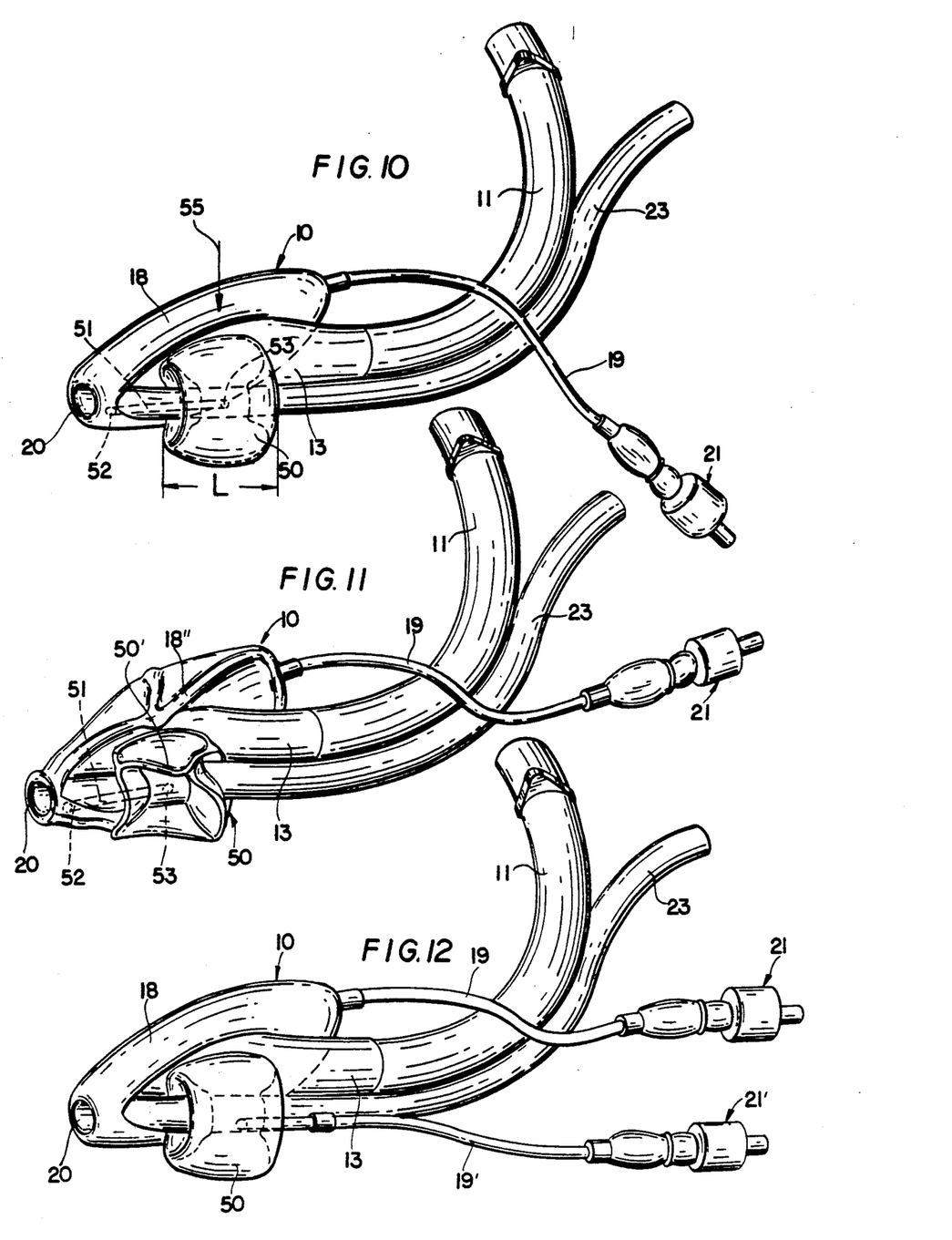
FIG. 10 is a rear three-quarter perspective view of another preferred embodiment of the invention, shown inflated.
FIG. 11 is a similar view of the embodiment of FIG. 10, for the deflated condition thereof.
FIG. 12 is a view similar to FIG. 10, for a modification of the embodiment of FIG. 10.

The second, and now more greatly, preferred embodiment of the invention is shown in FIGS. 10 and 11 and may be identical to the embodiment of FIGS. 1 to 4 except for the addition of a second inflatable cuff 50; all other parts of FIGS. 10 and 11 may be as described for FIGS. 1 to 4 and therefore the same reference numbers are used, where applicable. Cuff 50 is seen to be of longitudinal extent L which is suitably one-third to one-half the longitudinal extent of the mask body 13, and cuff 50 is located intermediate the longitudinal ends of the mask body. Cuff 50 effectively surrounds that circumferential part of the evacuation tube 23 which is exposed either circumferential side of tube 23 assembly to the mask body 13. In FIG. 10, inflation/deflation airflow to and from cuff 50 is provided by a small tubular passage 51 that is locally integrated into the structure of the evacuation tube 23; passage 51 has ported distal connection at 52 to the inflatable ring 18 of mask 10, and ported proximal connection at 53 to the inner volume of cuff 50. The same pressure of inflation air via line 19 thus simultaneously serves ring 18 and cuff 50.

One way to manufacture and assemble cuff 50 to mask 10 is to initially form cuff 50 as a circumferentially continuous subassembly with the drainage tube 23, complete with passage 51 and its ported connection 53 to the inner volume of cuff 50. Thereafter, upon assembly of this subassembly 23/50 to the backside of the mask body 13, the ported connection 52 of passage 51 is completed to the inner volume of inflatable ring 18, and cementing along the course of adjacency of tube 23 and body 13 renders the assembly permanent. In the process of such assembly the portion of cuff 50 adjacent body 13 is squashed, but the assembled cuff 50 survives as a large inflatable arc around the exposed remaining girth of tube 23.

Preferably, the material of cuff 50 is of lesser thickness or of softer material, and therefore more softly compliant than the material of ring 18. This fractional-gauge relationship, between the material of cuff 50 and the material of ring 18 is evident from FIG. 11, wherein for the deflated condition of the mask, the wrinkles and folds of cuff 50 (as at 50') are seen to be much more thin and narrow than the wrinkles and folds (as at 18Δ) of ring 18. In fact, the bulk of cuff 50 in deflated condition is virtually zero, so that, for a given patient, insertion and removal of the structure of FIG. 11 is negligibly different from similar use of the structure of FIGS. 1 to 4.

On the other hand, having been inserted in a patient in the manner described for FIGS. 1 to 4, inflation of the device of FIGS. 10 and 11 is found to provide notable improvement in peripheral sealing efficacy, for mask ring 18 around the laryngeal inlet. And this sealing efficacy is achieved for a substantially reduced inflation pressure, as compared with data given above for the embodiment of FIGS. 1 to 4. Specifically, the most suitable intra-cuff inflation pressure thus far experimentally established for the embodiment of FIGS. 10 and 11 is approximately 62 cm H₂O, which will be recognized as very substantially less than the 80 to 160-mm Hg levels described above for the embodiment of FIGS. 1 to 4.

The significance of the improvement realized by the embodiment of FIGS. 10 and 11 will appear from a short discussion, which of course must involve a comparison with earlier inflatable-ring structures, as at 18 in FIGS. 1 to 4, or as in the patents mentioned above.

In the earlier structures, inflation of the ring of the laryngeal mask expands the space around it, at the laryngeal inlet, but posteriorly the relatively hard mask body or "backplate" is forced in a rather unyielding manner against the back of the throat. When a drainage tube is added, as at 23 in FIGS. 1 to 4, the drainage tube lies wedged between the backplate and the throat, further increasing the potential discomfort and trauma which may be produced, especially in a prolonged use. By using the second cuff 50 (FIGS. 10 and 11), trauma potential is substantially reduced, not only because inflation pressures are reduced but also because the soft texture and pressure distribution afforded by cuff 50 against the backwall of the pharynx inherently cushions the backwall reference and avoids drainage-tube (23) contact with the backwall of the pharynx.

Normally, i.e., for a prior inflatable mask ring (18), without cuff 50, leaks may be expected to occur when gas is forced into the lungs at pressures exceeding 2kPa (20 cm H₂O), and I have identified the location of such leaks to be at approximately the longitudinal mid-point of the mase ring (18) and on either or both sides of the mask when viewed anteriorly; on the anterior side that is viewable in FIG. 10, such a leak point is approximated by the head end of an arrow 55. Due to this general location of a potential leak point, the new softly compliant inflatable cuff 50 is placed behind the mask and at the same general longitudinal location, so that when inflated, cuff 50 will forwardly urge the laryngeal mask 10 and its inflated ring 18 at the most advantageous region to prevent leaks.

A further advantage in the structure of FIGS. 10 and 11 is the discovery that peripherally sealed engagement of ring 18 to the laryngeal inlet is now possible for substantially reduced inflation pressures. The ring 18 is necessarily of greater wall thickness than that of cuff 50 because of the need to assure against accidental herniation of the wall during use, causing an obstruction to breathing; the reduced necessary inflation pressure thus materially reduces the chance of a herniation in the wall of ring 18. At the same time, the wall thickness of cuff 50 is preferably much less, for example, one-third to one-half the wall thickness of ring, because the consequences of herniation of the wall of cuff 50 are in no sense to be compared to a herniation of ring 18; furthermore, by using a thinner-walled, i.e., more compliant, material for cuff 50, the cuff 50 inflates more readily and is able to forwardly thrust and displace the mask for enhanced seal development to the laryngeal perimeter, before full inflation pressure is developed.

There is some evidence suggesting that the high pressures which may develop in ring 18, during anaesthesia, due to absorption of anaesthetic gases, can cause a reflex relaxation of the oesophagus, making regurgitation more likely. The thinner and therefore more yieldable material of cuff 50 acts as a pressure-limiting system, preventing development of such high pressures in ring 18.

As a further advantage of the structure of FIGS. 10 and 11, it is found that by requiring less inflation pressure within ring 18, it has become possible for ring 18 to conform itself more closely to the complex contours of the laryngeal perimeter, instead of stretching tightly against them. This circumstance avoids the development of high-pressure points and yields a more favorable ratio of intra-ring (18) pressure to laryngeal-inlet seal pressure Preliminary experiments have shown a mean leak-developing pressure of 32 cm H₂O, for an intra-ring (18) pressure of 60 cm H₂O; and this is to be compared with use of an inflated ring 18 without cuff 50, wherein a leak-developing pressure is encountered at about 18 cm H₂O, for the same intra-ring (18) pressure.

The embodiment of FIG. 12 differs from that of FIGS. 10 and 11, solely in the fact that separate provision is made at 21 (and line 19) for inflation of ring 18 apart from separate provision at 21' (and line 19') for inflation of cuff 50. This feature will be understood to provide a degree of flexibility in respect to selective choice of different inflation pressures to determine a possible optimum for the inflation pressure at 18, as compared with the inflation pressure at 50. All other features of FIG. 12 are as described for FIGS. 10 and 11.

All of the foregoing sealing advantages of the structures of FIGS. 10 and 11, and of FIG. 12, are achieved without degrading the drainage-seal engagement to the upper sphinctral region of the oesophageal inlet.

While it is noted above that in the embodiment of FIGS. 1 to 5 that the airway tube 11 is preferably rigid to permit use of a manipulating handle, it should be clear that relative rigidity is desired in all embodiments of the invention. And it has been found that in situations in which the two tubes 11 and 23 are adhesively united with conforming and nested adjacent curvatures, as by using a silicone adhesive along the curved course of their adjacency, with the central axes of both tubes in the same plane, a sufficient rigidity can be achieved for the adhesively bonded and thus-nested assembly of the two curved tubes, without necessarily having to additionally rely on metal reinforcement.

What is claimed is:

1. An artificial airway device to facilitate a patient's lung ventilation, comprising an airway tube, an evacuation tube, and a laryngeal mask at one end of said tubes, said mask including a first inflatable-cuff formation of flexible material in a generally elliptical configuration having from a proximal end to a distal end and in generally a single plane which is inclined to the axis of the airway tube at the distal end of the airway tube, a second inflatable-cuff formation carried by said mask on the posterior side of said plane, said mask being configured upon inflation of said cuff formations (1) to form a seal of said airway tube solely around the circumference of the laryngeal inlet and (2) to establish a cushioning action via said second cuff formation between the posterior side of said mask and the posterior wall of the pharynx, the distal end of said cuff formation being configured for entry into and insertional location of said device by engagement with the oesophagus at the upper sphinctral region of the oesophagus when the mask is positioned for sealing the airway tube to the laryngeal inlet, said evacuation tube having an open distal end centrally within and axially short of the distal end of said first cuff formation, inflation-passage means communicating with both said inflatable cuff formations for selective inflation/deflation operation of said cuff formations, whereby (1) to seal said airway tube for communication solely with the laryngeal inlet, (2) to cushion the reference of said mask to the posterior wall of the pharynx, and (3) to seal said evacuation tube solely to the sphinctral region, so that upon evacuation of said evacuation tube after inflation into sealed relation with the sphinctral region of the oesophagus adjacent oesophagus tissue will be induced to locally displace into enhanced sealing engagement with the inflated distal cuff formation, whereby gastric-discharge products can pass only by way of said evacuation tube, thus reducing any chance of gastric leakage into the laryngeal inlet.

2. An artificial airway device to facilitate a patient's lung ventilation, comprising an airway tube, an evacuation tube, and a laryngeal mask at one end of said tubes, said mask being of generally elliptical configuration having from a proximal end to a distal end and in generally a single plane, said configuration being adapted for support by and around the laryngeal inlet and orienting the distal end of the airway tube at an angle to said plane and in substantial alignment with the axis of the laryngeal inlet when supported by and around the laryngeal inlet, the distal end of said mask having a first cuff formation configured for entry into and insertional location of said device by engagement with the upper sphinctral region of the oesophagus when the mask is positioned for airway-tube alignment with the axis of the oesophagus inlet, said evacuation tube having an open distal end centrally within and axially short of the distal end of said first cuff formation, a second inflatable-cuff formation carried by said mask on the posterior side of said plane, and inflation-passage means communicating with both said cuff formations.

3. An artificial airway device to facilitate a patient's lung ventilation, comprising an airway tube, a suction tube, and a laryngeal mask at one end of said tubes, said mask having a proximal end and a distal end and being configured to form a seal of said airway tube solely around the circumference of the patient's laryngeal inlet, said distal end being configured for entry into and insertional location of said device at the entrance of the upper sphinctral region of the oesophagus when said mask is positioned for sealing the airway tube to the laryngeal inlet, said evacuation tube having an open distal end centrally within but axially short of the distal end of said mask, and the distal end of said mask including a first inflatable flexible cuff formation for peripherally sealed engagement of the upper sphinctral region to the distal end of said evacuation tube, thus exposing a passage via said mask for airway-tube communication solely with the laryngeal inlet on the anterior side of said mask, while exposing the posterior side of said mask to the posterior wall of the pharynx, a second inflatable-cuff formation carried by the posterior side of said mask for inflated engagement to the posterior wall of the pharynx, and inflation-passage means communicating with both said cuff formations.

4. The artificial airway device of claim 3, in which the laryngeal mask includes an inflatable ring for establishing a seal around the laryngeal inlet and in which said first inflatable cuff formation is the distal portion of the inflatable ring of the laryngeal mask.

5. The artificial airway device of claim 1 or claim 2 or claim 3, in which said airway tube is relatively rigid and curved to follow the airway of a patient.

6. The artificial airway device of claim 1 or claim 2 claim 3, in which said airway tube is relatively rigid and curved to follow the airway of a patient, and an externally projecting substantially rigid handle portion mounted to the end of the airway tube remote from the mask.

7. The artificial airway device of claim 1 or claim 2 or claim 3, in which said airway tube is relatively rigid and curved to follow the airway of a patient, and an externally projecting substantially rigid handle portion detachably connected to the end of the airway tube remote from the mask.

8. The artificial airway device of claim 1 or claim 2 or claim 3, in which said airway tube is relatively rigid and curved to follow the airway of a patient, the bore of said airway tube being of a diameter to selectively accommodate and guide the insertion of an inflatably cuffed endotrachial tube, with the inflatable cuff of the endotrachial tube being insertable through and beyond said mask, for cuffed selective intubation-sealing engagement to the larynegeal inlet at a location which is distal beyond said mask.

9. The artificial airway device of claim 1 or claim 2 or claim 3, in which said evacuation tube is circumferentially reinforced at least in the region of cuff inflation, whereby to avoid evacuation-tube collapse by reason of cuff inflation.

10. The method of installing an artificial airway device to facilitate a patient's lung ventilation, wherein the method comprises the steps of:
  (a) providing an inflatably sealed laryngeal mask at the end of an airway tube, wherein a first inflatable cuff formation is carried on the posterior side of the mask, and wherein the distal end of said mask includes an inflatable-cuff cuff formation for sealed engagement to the upper sphinctral region of the oesophagus, and wherein an evacuation tube has an open distal end terminating within said cuff formation;
  (b) inserting said device, in deflated condition to position the distal end of the mask in the sphinctral region of the oesophagus, with the mask positioned for support around the laryngeal inlet, and with posterior side of the mask in confronting relation with the posterior wall of the pharynx;
  (c) inflating both said cuff formations to establish a mask seal around the laryngeal inlet with cushioned reference to the posterior wall of the pharynx, as well as a cuff seal of the evacuation tube within the upper sphinctral region of the oesophagus; and
  (d) establishing a reduced-pressure suction connection to the evacuation tube, whereby to enhance cuff-formation seal action to tissues of the upper-sphinctral region.

11. The method of installing an artificial airway device to facilitate a patient's lung ventilation, wherein the method comprises the steps of:

(a) providing a laryngeal mask at the distal end of an airway tube, wherein the mask is adapted for support around the laryngeal inlet such as to align the distal end of the airway tube with the laryngeal inlet when the distal end of the mask engages the upper sphinctral region of the oesophagus, wherein a first inflatable-cuff formation at the distal end of the mask engages within the upper sphinctral region upon achievement of said alignment of the airway tube with the laryngeal inlet, wherein a second inflatable-cuff formation carried on the posterior side of said mask is poised for inflated interposition between said mask and the posterior wall of the pharynx, and wherein an evacuation tube has an open distal end terminating within said cuff formation; said method comprising the steps of:

(b) inserting said device, in deflated condition to position the distal end of the mask in the sphinctral region of the oesophagus, and with the mask positioned for support around the laryngeal inlet;

(c) inflating said cuff formations to establish a cuff seal of the evacuation tube within the upper sphinctral region of the oesophagus and to establish a cushioning reference on the posterior side of the mask with respect to the posterior wall of the pharynx, and with pressurized loading of the mask toward the laryngeal inlet; and (d) establishing a reduced-pressure suction connection to the evacuation tube, whereby to enhance cuff-formation seal action to tissues of the upper-sphinctral region.

12. The method of claim 10 or claim 11, comprising the additional step of observing suction pressure for retention at a predetermined reduced-pressure level, thus confirming that seal action to the oesophagus is complete.

13. The method of claim 10 or claim 11, comprising the additional step of maintaining a predetermined reduced-pressure level in said evacuation tube for the duration of lung ventilation via the airway tube.

14. An artificial airway device to facilitate a patient's lung ventilation, comprising an airway tube and a laryngeal mask at one end of said tube, said mask including a first inflatable-cuff formation of flexible material in a generally elliptical configuration extending from a proximal end to a distal end and in generally a single plane which is inclined to the axis of the airway tube at the distal end of the airway tube and on the posterior side of said plane, a second inflatable-cuff formation carried by the distal side of said mask in a region intermediate said ends, and inflation-passage means communicating with both said inflatable-cuff formations.

15. The artificial airway device of claim 1 or claim 2 or claim 3 or claim 14, in which said inflation-passage means comprises a single flexible-tube connection to said mask.

16. The artificial airway device of claim 1 or claim 2 or claim 3 or claim 14, in which said inflation-passage means comprises first and second flexible tube connections independently and respectively in communication with said first and second cuff formations.

17. The artificial airway device of claim 14, in which the wall thickness of said first inflatable-cuff formation exceeds the wall thickness of said second inflatable-cuff formation.

18. The artificial airway device of claim 17, in which the extent to which wall thickness of said first inflatable-cuff formation exceeds the wall thickness of said second inflatable-cuff formation is in the range 2:1 to 3:1.

19. The artificial airway device of claim 14, in which the wall of said second inflatable-cuff formation is more compliant than the wall of said first inflatable-cuff formation.

20. An artificial airway device to facilitate a patient's lung ventilation, comprising an airway tube, an evacuation tube and a laryngeal mask at one end of said tubes, said mask including an inflatable annular cuff of flexible material in a generally elliptical configuration which is in generally a single plane, said generally elliptical configuration having a major axis extending from a proximal airway-tube connection end of said cuff to a distal end of said cuff, said single plane being inclined to the axis of the airway tube at airway-tube connection to said mask, said mask being configured upon inflation to form a seal of said airway tube solely around the circumference of the laryngeal inlet, the distal end of said cuff in deflated condition being configured for entry into and insertional positioning of said device by engagement within the upper sphinctral region of the oesophagus when the mask is positioned for sealing the airway tube to the laryngeal inlet, said evacuation tube having sealed passage within a portion of said cuff and having an open distal end (a) which is peripherally sealed to and (b) which is surrounded by inflatable material of the distal end of said cuff, and means including a third tube communicating with said inflatable cuff for selective inflation/deflation operation of said cuff (1) for sealing said airway tube to communicate solely with the laryngeal inlet and (2) for peripherally sealing said evacuation tube solely to the upper sphinctral region; whereby, upon evacuation of said evacuation tube after cuff inflation into peripherally sealed relation with the upper sphinctral region of the oesophagus, adjacent oesophagus tissue will be induced to locally displace into enhanced sealing engagement with the inflated cuff, whereby gastric-discharge products can pass only by way of said evacuation tube, thus reducing any chance of gastric leakage into the laryngeal inlet.

21. An artificial airway device to facilitate a patient's lung ventilation, comprising an airway tube, an evacuation tube, and a laryngeal mask at one end of said tubes, said mask being of generally elliptical configuration which is in generally a single plane, said generally elliptical configuration having a major axis extending from a proximal airway-tube connection end of said mask to a distal end of said mask, said single plane being inclined to the axis of the airway tube at airway-tube connection to said mask, said configuration being adapted for peripherally sealed support by and around the laryngeal inlet and orienting the distal end of the airway tube at an angle to said plane and in substantial alignment with the axis of the laryngeal inlet when supported by and around the laryngeal inlet, the distal end of said mask having an inflatable cuff formation of flexible material configured for entry into and insertional positioning of said device by engagement within the upper sphinctral region of the oesophagus when the mask is positioned for airway-tube alignment with the axis of the laryngeal inlet, said evacuation tube having sealed passage within a portion of said cuff formation and having an open end that is (a) peripherally sealed to and (b) surrounded by inflatable material of said cuff at the distal end of said mask, means including a third tube communicating with said inflatable cuff formation for selective inflation/deflation operation of said cuff formation, whereby to peripherally seal said evacuation tube solely to the upper sphinctral region, so that upon evacuation of said evacuation tube after cuff inflation into peripherally sealed relation with the sphinctral region of the oesophagus, adjacent oesophagus tissue will be induced to locally displace into enhanced sealing engagement with the inflated-cuff formation, whereby gastric-discharge products can pass only by way of said evacuation tube, thus reducing any chance of gastric leakage into the laryngeal inlet.

22. An artificial airway device to facilitate a patient's lung ventilation, comprising an airway tube, a suction tube, and a laryngeal mask at one end of said tubes, said mask being configured to form a seal of said airway tube in generally a single plane and around the circumference of the patient's laryngeal inlet, said mask having an elongate axis of symmetry in said plane extending from a proximal airway-tube connection end of said mask to a distal end of said mask, said single plane being inclined to the axis of the airway tube at airway-tube connection to said mask, the distal end of said mask including an inflatable flexible cuff formation for peripherally sealed engagement to the upper sphinctral region, said distal end being configured for entry into and insertional positioning of said device within the entrance of the upper sphinctral region of the oesophagus when said mask is positioned for sealing the airway tube to the laryngeal inlet, said evacuation tube having sealed passage within a portion of said cuff formation and having an open end that is peripherally sealed to and surrounded by inflatable material of said cuff at the distal end of said mask, and means including a third tube communicating with said cuff formation for selective inflation of said cuff formation into peripherally sealed engagement with the inlet to the upper sphinctral region; whereby, upon evacuation of said evacuation tube after cuff inflation into engaged relation with the inlet to the upper sphinctral region, tissues adjacent said engaged relation will locally displace into enhanced sealing engagement with the inflated cuff formation, so that gastric-discharge products can pass only by way of said evacuation tube, thus reducing any chance of gastric leakage into the laryngeal inlet.

23. The artificial airway device of claim 22, in which the laryngeal mask includes an inflatable ring for establishing a seal around the laryngeal inlet and in which said inflatable cuff formation is a portion of the inflatable ring of the laryngeal mask.

24. The artificial airway device of claim 20 or claim 21 or claim 22, in which said airway tube is relatively rigid and curved to follow the airway of a patient.

25. The artificial airway device of claim 20 or claim 21 or claim 22, in which said airway tube is relatively rigid and curved to follow the airway of a patient, and an externally projecting substantially rigid handle portion mounted to the end of the airway tube remote from the mask.

26. The artificial airway device of claim 20 or claim 21 or claim 22, in which said airway tube is relatively rigid and curved to follow the airway of a patient, and an externally projecting substantially rigid handle portion detachably connected to the end of the airway tube remote from the mask.

27. The artificial airway device of claim 20 or claim 21 or claim 22, in which said airway tube is relatively rigid and curved to follow the airway of a patient, the bore of said airway tube being of a diameter to selectively accommodate and guide the insertion of an inflatably cuffed endotrachial tube, with the inflatable cuff through and beyond said mask, for cuffed selective intubation-sealing engagement to the laryngeal inlet at a location which is distal beyond said mask.

28. The artificial airway device of claim 20 or claim 21 or claim 22, and a second evacuation tube, said two tubes conforming in angularly spaced relation to said airway tube and being interconnected at said mask to constitute a single tube having said open distal end.

29. The artificial airway device of claim 20 or claim 21 or claim 22, and a second airway tube, said two airway tubes being in side-by-side adjacency and interconnected at said mask to constitute a single distal-end airway passage for generally axial alignment with the axis of the laryngeal inlet.

30. The artificial airway device of claim 20 or claim 21 or claim 22, in which said evacuation tube is circumferentially reinforced at least in the region of cuff inflation, whereby to avoid evacuation-tube collapse by reason of cuff inflation.

31. The method of facilitating a patient's lung ventilation, which method comprises the steps of:

(a) providing an artificial airway device which comprises an inflatable sealed laryngeal mask at the end of an airway tube, said mask including an inflatable-cuff formation for sealed engagement to the upper sphinctral region of the oesophagus, and an evacuation tube having sealed passage within said cuff formation and having an open distal end which is peripherally sealed to and surrounded by inflatable material of the distal end of the cuff formation;

(b) inserting said device, in deflated condition to position the distal end of the mask in the sphinctral region of the oesophagus, and with the mask positioned for support around the laryngeal inlet;

(c) inflating said mask and cuff formation to establish a mask seal around the laryngeal inlet and a cuff seal of the evacuation tube within and to the upper sphinctral region of the oesophagus; and (d) establishing a reduced-pressure suction connection to the evacuation tube, whereby to enhance cuff-formation seal action to tissues of the upper-sphinctral region.

32. The method of facilitating a patient's lung ventilation, which method comprises the steps of:

(a) providing an artificial airway device which comprises a laryngeal mask having a proximal end engaged to an end of an airway tube, the mask having a distal end and being adapted for support around the laryngeal inlet such as to align the engaged end of the airway tube with the laryngeal inlet when the distal end of the mask engages within the upper sphinctral region of the oesophagus, an inflatable-cuff formation at the distal end of the mask engaging within the upper sphinctral region upon achievement of said alignment of the airway tube with the laryngeal inlet, and an evacuation tube having (i) sealed passage within said cuff formation and having (ii) an open distal end which is peripherally sealed to and surrounded by inflatable material of the cuff formation at the distal end of the mask;

(b) inserting said device, in deflated condition to position the distal end of the mask in the upper sphinctral region of the oesophagus, and with the mask positioned for support around the laryngeal inlet;

(c) inflating said cuff formation to establish a cuff seal of the evacuation tube within the upper sphinctral region of the oesophagus; and (d) establishing a reduced-pressure suction connection to the evacuation tube, whereby to enhance cuff-formation seal action to tissues of the upper-sphinctral region.

33. The method of claim 31 or claim 32, comprising the additional step of observing suction pressure for retention at a predetermined reduced-pressure level, thus confirming that seal action to the oesophagus is complete.

34. The method of claim 31 or claim 32, comprising the additional step of maintaining a predetermined reduced-pressure level in said evacuation tube for the duration of lung ventilation via the airway tube.

* * * * *

UNITED STATES PATENT AND TRADEMARK OFFICE
CERTIFICATE OF CORRECTION

PATENT NO. : 5,241,956

DATED : September 7, 1993

INVENTOR(S) : Archibald I. J. Brain

It is certified that error appears in the above-indentified patent and that said Letters Patent is hereby corrected as shown below:

On the Title page, bottom of Column 2 "19 claims" should read -- 34 claims --, as shown on attached page.

Signed and Sealed this

Twenty-ninth Day of March, 1994

Attest:

BRUCE LEHMAN

Attesting Officer

Commissioner of Patents and Trademarks

United States Patent [19]

Brain

[11] Patent Number: 5,241,956
[45] Date of Patent: Sep. 7, 1993

[54] LARYNGEAL MASK AIRWAY WITH CONCENTRIC DRAINAGE OF OESOPHAGUS DISCHARGE

[76] Inventor: Archibald I. J. Brain, St. Andrews, Abney Court Drive, Bourne End, Bucks, United Kingdom

[21] Appl. No.: 952,586

[22] Filed: Sep. 28, 1992

Related U.S. Application Data

[63] Continuation-in-part of Ser. No. 919,289, Jul. 24, 1992.

[30] Foreign Application Priority Data

May 21, 1992 [GB] United Kingdom ............... 9210854
Jul. 23, 1992 [GB] United Kingdom ............... 9215650

[51] Int. Cl.$^5$ ............................................. A61M 16/00
[52] U.S. Cl. ............................ 128/207.15; 128/207.14; 604/174; 604/96
[58] Field of Search ................... 128/207.14, 207.15, 128/206.26, 207.16, 200.26; 604/96–103, 174

[56] References Cited

U.S. PATENT DOCUMENTS

| | | | |
|---|---|---|---|
| 4,454,887 | 6/1984 | Krüger | 128/772 |
| 4,497,318 | 2/1985 | Donmichael | 128/202.28 |
| 4,969,458 | 11/1990 | Wiktor | 606/194 |
| 4,981,470 | 1/1991 | Bombeck, IV | 128/635 |
| 4,995,388 | 2/1991 | Brain | 128/207.15 |
| 5,033,466 | 7/1991 | Weymuller | 128/207.15 |
| 5,038,766 | 8/1991 | Parker | 128/200.26 |
| 5,067,497 | 11/1991 | Greear | 128/207.15 |
| 5,076,268 | 12/1991 | Weber | 128/207.15 |
| 5,116,305 | 5/1992 | Milder | 600/18 |

FOREIGN PATENT DOCUMENTS

| | | | |
|---|---|---|---|
| 2111394 | 7/1983 | United Kingdom | 128/207.15 |
| 2171017 | 8/1986 | United Kingdom | 128/207.15 |
| 2229367 | 9/1990 | United Kingdom | 128/207.15 |

Primary Examiner—Edgar S. Burr
Assistant Examiner—Eric P. Raciti
Attorney, Agent, or Firm—Hopgood, Calimafde, Kalil, Blaustein & Judlowe

[57] ABSTRACT

A laryngeal mask airway is described which is fitted with an evacuation or drainage tube which passes through the back of the mask and terminates concentrically within an inflatable-cuff formation at the distal end of the mask. In the case of a laryngeal mask which relies on an inflatable ring to establish a seal around the laryngeal inlet, the inflatable-cuff formation results from sealed passage of the evacuation tube through the distal region of the inflatable ring, the distal end of which is centrally apertured and reentrantly folded into sealed junction with the distal end of the tube. When the mask is inflated, its distal end establishes a cuff, sealing the tube against the upper oesophageal sphincter. In the presently preferred embodiment, an auxiliary inflatable cuff is carried at the back side of the mask and, when inflated, establishes a cushioned reference between the evacuation tube and the posterior wall of the pharynx, enabling more effective sealing of the mask to the laryngeal inlet and of the drainage cuff to the oesophageal sphincter, in the circumstance of negative pressure applied to the evacuation tube.

34 Claims, 3 Drawing Sheets